United States Patent [19]
Bocan

[11] Patent Number: 6,093,719
[45] Date of Patent: Jul. 25, 2000

[54] METHOD AND PHARMACEUTICAL COMPOSITION FOR REGULATING LIPID CONCENTRATION

[75] Inventor: Thomas M. A. Bocan, Ann Arbor, Mich.

[73] Assignee: Warner-Lambert Company, Morris Plains, N.J.

[21] Appl. No.: 09/345,944

[22] Filed: Jul. 1, 1999

Related U.S. Application Data

[62] Division of application No. 09/051,368, filed as application No. PCT/US96/15854, Oct. 2, 1996.
[60] Provisional application No. 60/006,155, Nov. 2, 1995.
[51] Int. Cl.$^7$ .......................... A61K 31/18; A61K 31/16; A61K 31/435; A61K 31/405; A61K 31/40; A61K 31/35; A61K 31/225
[52] U.S. Cl. .......................... 514/277; 514/415; 514/423; 514/460; 514/547; 514/601; 514/602; 514/603; 514/604; 514/625
[58] Field of Search .................................. 514/277, 415, 514/423, 460, 547, 601, 602, 603, 604, 625

[56] References Cited

FOREIGN PATENT DOCUMENTS

| | | |
|---|---|---|
| 0373507 | 6/1990 | European Pat. Off. |
| 0475148 | 3/1992 | European Pat. Off. |
| 9409774 | 5/1994 | WIPO . |
| 9426702 | 11/1994 | WIPO . |
| 9513063 | 5/1995 | WIPO . |

OTHER PUBLICATIONS

Sliskovic and Trivedi, "ACAT Inhibitors: Potential Anti--atherosclerotic Agents", *Current Medicinal Chemistry*, vol. 1, 1994, 204–225.

LaRosa et al., "The Cholesterol Facts, A Summary of the Evidence Relating Dietary Fats, Serum Cholesterol, and Coronary Heart Disease", *Circulation*, vol. 81, No. 5, 1990, 1721–1733.

Gordon et al., "High Density Lipoprotein As a Protective Factor Against Coronary Heart Disease", *The American Journal of Medicine*, vol. 62, 1977, 707–714.

Frick et al., "Helsinki Heart Study: Primary–Prevention Trial With Gemfibrozil in Middle–Aged Men with Dyslipidemia", *The New England Journal of Medicine*, vol. 317, No. 20, 1987, 1237–1245.

PCT International Search Report, PCT/US96/15854.

Heinonen et al., "Atorvastatin, a New HMG–CoA Reductase Inhibitor as Monotherapy and Combined with Colestipol", *J. Cardiovasc. Pharmacol. Therapeut.*, vol. 1, No. 2, 1996, 117–122.

Kusunoki et al., "Studies on Acyl–CoA:Cholesterol Acyltransferase (ACAT) Inhibitory Effects and Enzyme Selectivity of F–1394, a Pantotheic Acid Derivative", *Jpn. J. Pharmacol.*, vol. 67, 1995, 195–203.

Davignon, "Prospects for Drug Therapy for Hyperlipoproteinaemia" *Diabete & Metabolisme*, vol. 21, No. 2, 1995, 139–146.

Ed. J.E.F. Reynolds, "Martindale, the extra pharmacopoeia", *The Pharmaceutical Press*, London, 987–989 (1993).

CA 110:128422, Osborne et al, 1989.

*Primary Examiner*—Kimberly Jordan
*Attorney, Agent, or Firm*—Elizabeth M. Anderson

[57] ABSTRACT

The present invention is a combination of an ACAT inhibitor, for example, sulfamic acid, [[2,4,6-tris(1-methylethyl)phenyl]acetyl]-, 2,6-bis(1-methylethyl) phenyl ester, and an HMG-CoA-reductase inhibitor, for example, atorvastatin, effective for lipid regulation. The combination of agents results in a greater reduction in plasma VLDL and LDL cholesterol and increases HDL cholesterol than either alone resulting in a less atherogenic lipoportein profile. The combination is useful in the treatment of patients with or at risk of developing ischemic syndromes in order to restore endogenous vascular endothelium-dependent activities.

3 Claims, No Drawings

METHOD AND PHARMACEUTICAL COMPOSITION FOR REGULATING LIPID CONCENTRATION

CROSS-REFERENCE TO RELATED APPLICATIONS

This is a divisional of U.S. Ser. No. 09/051,368, filed Apr. 7, 1998, which is a national filing of PCT/US96/15854, filed Oct. 2, 1986; priority based on Provisional Application No. 60/006,155, filed Nov. 2, 1995.

BACKGROUND OF THE INVENTION

The treatment of patients with or at risk of developing ischemic syndromes with doses of an HMG-CoA reductase inhibitor to lower total and LDL cholesterol is known. This is done in order to restore endogenous vascular endothelium-dependent activities including, but not limited to vasodilatory responses modulating vascular tone and blood flow, antiadherent properties of the blood vessel wall, and anticoagulation of platelets (International Publication Number WO 95/13063).

There is evidence from animal models that compounds which inhibit the enzyme, acyl-coenzyme A:cholesterol acyltransferase (ACAT) will be effective anti-atherosclerotic agents, (*Curr. Med. Chem.*, 1994;1:204–225). It is well-established that when the majority of cholesterol in plasma is carried on apolipoprotein B-containing lipoproteins, such as low-density lipoproteins (LDL-C) and very-low-density lipoproteins (VLDL-C), the risk of coronary artery disease in man is increased (*Circulation*, 1990;81:1721–1733). Conversely, high levels of cholesterol carried in high-density lipoproteins (HDL-C) is protective against coronary artery disease (*Am. J. Med.*, 1977;62:707–714). Thus, a drug which reduces the levels of atherogenic LDL-C and VLDL-C and elevates levels of protective HDL-C will produce a less atherogenic lipoprotein profile and thus a beneficial effect on atherosclerotic disease and its complications. This beneficial effect was demonstrated in man in the Helsinki Heart Study with the lipid regulator gemfibrozil which decreased LDL-C, increased HDL-C, and reduced the incidence of coronary artery disease (*N. Engl. J. Med.*, 1987;317:1237–1245).

SUMMARY OF THE INVENTION

We have now shown that a combination of ACAT inhibitor and HMG-CoA reductase inhibitor when administered in a chow/fat diet results in a greater reduction in apo B-containing liproprotein than either alone and that a normalization of the plasma lipoprotein profile can be achieved. This means the combination treatment results in plasma lipoprotein profile associated with a decreased risk of coronary artery disease.

We have also shown that a combination of ACAT inhibitors and HMG-CoA reductase inhibitors reduces the cholesteryl esters (CE) enrichment of pre-existing atherosclerotic lesions to the same extent as the HMG-CoA reductase inhibitor alone but that the histologic character of the atherosclerotic lesions is less complicated. This means that the lesions are less prone to induce myocardial infarction

DETAILED DESCRIPTION OF THE INVENTION

The novel method of treatment of this invention and the novel pharmaceutical compositions comprise the administration to a patient at risk of developing atherosclerosis or a patient in whom the disease has been diagnosed with an ACAT inhibitor and HMG-CoA reductase inhibitor which will restore endogenous vascular endothelium-dependent activities including improving the normal dilation capacity of the endothelium. This method may be used to induce vasodilation to modulate vascular tone and blood flow. Other improvements in vascular endothelium-dependent activities include decreasing the adherent properties of the blood vessel walls and decreasing the coagulation of platelets. Suitable subjects for the method of the present invention include those individuals who currently exhibit symptoms of atherosclerosis and those who are at risk of developing various acute ischemic syndromes including individuals with high blood pressure, diabetes, or hyperlipidemia, and individuals who smoke.

The various acute ischemic syndromes that may be treated by the method of the present invention include: angina pectoris, coronary artery disease (CAD), hypertension, cerebrovascular accidents, transient ischemic attacks, chronic obstructive pulmonary disease, chronic hypoxic lung disease, pulmonary hypertension, renal hypertension, chronic renal disease, microvascular complications of diabetes, and vaso-occlusive complications of sickle cell anemia.

An HMG-CoA reductase inhibitor for use in the novel method may be selected from atorvastatin, lovastatin, simvastatin, pravastatin, fluvastatin, and rivastatin; preferably atorvastatin, lovastatin, or simvastatin; most preferably atorvastatin.

HMG-CoA reductase inhibitors are known to function as antihypercholesterolemic agents. They reduce hepatic cholesterol biosynthesis by inhibiting the enzyme HMG-CoA reductase which catalyzes the early, rate-limiting step in the biosynthesis of cholesterol, the conversion of hydroxymethylglutarate to mevalonate. Known HMG-CoA reductase inhibitors include atorvastatin MEVACOR® (lovastatin), ZOCOR® (simvastatin), PRAVACHOL® (pravastatin), LESCOL® (fluvastatin), and rivastatin.

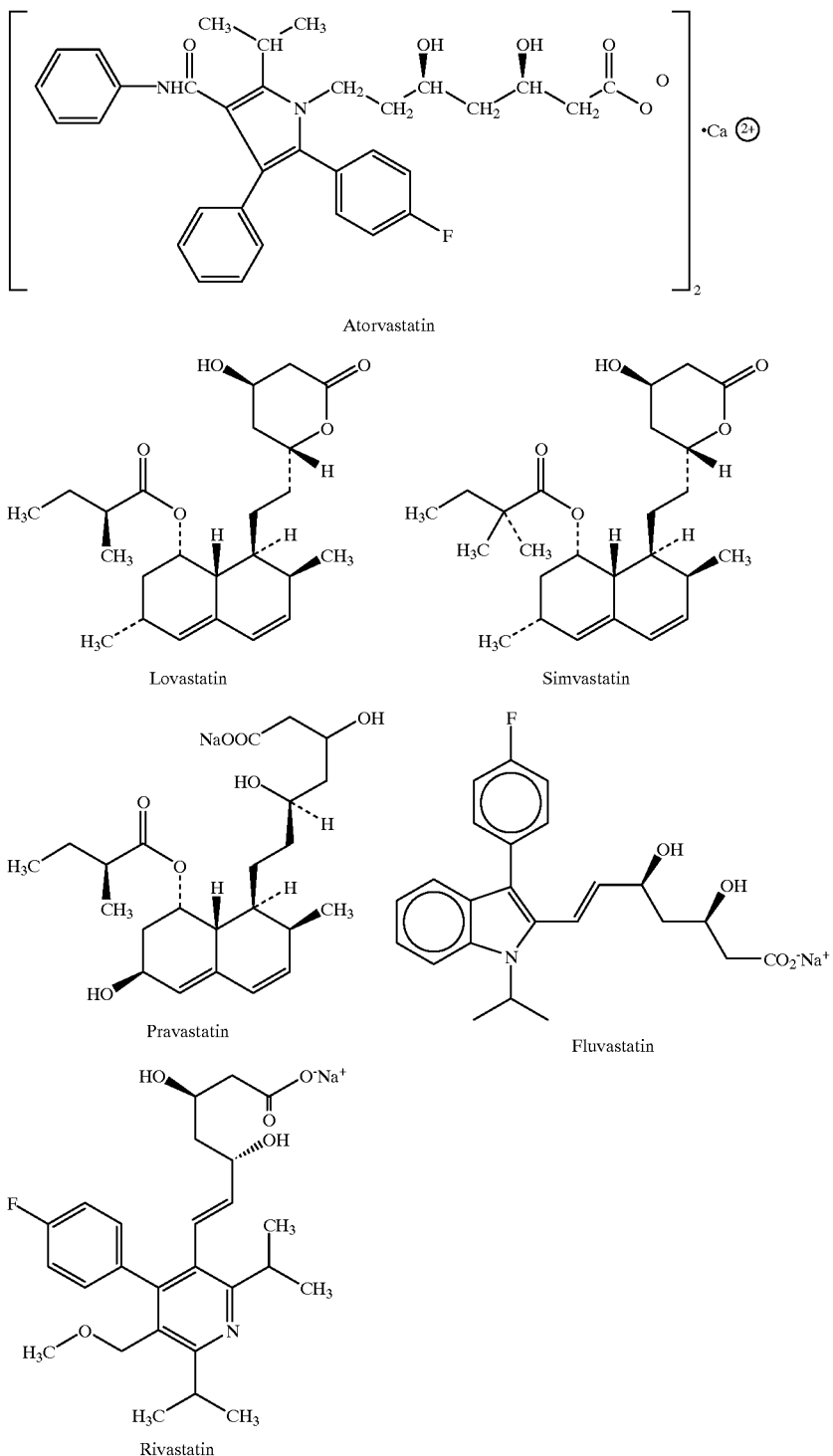

The doses of HMG-CoA reductase inhibitor contemplated for use in this invention are about 5 to 80 mg per day, preferably given in single or divided doses.

Preferably, the patient is placed on a prudent lipid-lowering diet during the treatment with the HMG-CoA reductase inhibitors.

Lipid lowering therapy with HMG-CoA reductase inhibitors normalizes vascular function in patients with hypercholesterolemia and/or coronary artery disease without the requirement for significant regression of the atherosclerotic lesions. The coronary microcirculation, which demonstrates significantly impaired endothelium dependent dilatory responses in the presence of hypercholesterolemia and atherosclerotic disease, but is usually free of atheroma, is likely to show marked improvement demonstrating the ability of lipid lowering therapy to halt the progression and/or promote regression of atherosclerosis in epicardial arteries in humans.

Atorvastatin is disclosed in U.S. Pat. No. 5,273,995. Related compounds are disclosed in U.S. Pat. No. 4,681,893.

Lovastatin and related compounds are disclosed in U.S. Pat. No. 4,231,938; simvastatin and related compounds are disclosed in U.S. Pat. No. 4,450,171 and U.S. Pat. No. 4,346,227; pravastatin and related compounds are disclosed in U.S. Pat. No. 4,346,227 and fluvastatin and related compounds are disclosed in U.S. Pat. No. 4,739,073; rivastatin and related compounds are disclosed in U.S. Pat. Nos. 5,177,080 and 5,006,530.

Compounds which effectively inhibit the enzyme, acyl-coenzyme A:cholesterol acyltransferase (ACAT) prevent the intestinal absorption of dietary cholesterol into the blood stream or the reabsorption of cholesterol which has been previously released into the intestine through the body's own regulatory action. The ACAT inhibiting compounds provide treatment of hypercholesterolemia and atherosclerosis. Such compounds include, for example, a compound of Formula I

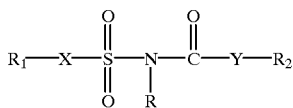

I or a pharmaceutically acceptable salt thereof wherein:

X and Y are selected from oxygen, sulfur and $(CR'R'')_n$, wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl;

with the proviso at least one of X and Y is $(CR'R'')_n$ and with the further proviso when X and Y are both $(CR'R'')_n$ and R' and R'' are hydrogen and n is one, $R_1$ and $R_2$ are aryl;

R is hydrogen, a straight or branched alkyl of from 1 to 8 carbon atoms or benzyl;

$R_1$ and $R_2$ are each independently selected from (a) phenyl or phenoxy each of which is unsubstituted or is substituted with 1 to 5 substituents selected from phenyl, an alkyl group having from 1 to 6 carbon atoms and which is straight or branched, an alkoxy group having from 1 to 6 carbon atoms and which is straight or branched;

phenoxy, hydroxy, fluorine, chlorine, bromine, nitro, trifluoromethyl,

—COOH,

—COOalkyl wherein alkyl has from 1 to 4 carbon atoms and is straight or branched, —$(CH_2)_p NR_3 R_4$ wherein p is zero or one, and each of $R_3$ and $R_4$ is selected from hydrogen or a straight or branched alkyl group having 1 to 4 carbon atoms;

(b) 1- or 2-naphthyl unsubstituted or substituted with from 1 to 3 substituents selected from phenyl, an alkyl group having from 1 to 6 carbon atoms and which is straight or branched, an alkoxy group having from 1 to 6 carbon atoms and which is straight or branched;

hydroxy, phenoxy, fluorine, chlorine, bromine, nitro, trifluoromethyl,

—COOH,

—COOalkyl wherein alkyl has from 1 to 4 carbon atoms and is straight or branched, —$(CH_2)_p NR_3 R_4$ wherein p, $R_3$ and $R_4$ have the meanings defined above;

(c) arylalkyl;

(d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms;

with the provisos:

(i) where X is $(CH_2)_n$, Y is oxygen, and $R_1$ is a substituted phenyl, then $R_2$ is a substituted phenyl;

(ii) where Y is oxygen, X is $(CH_2)_n$, $R^2$ is phenyl or naphthyl, then $R^1$ is not a straight or branched alkyl chain; and (iii) the following compounds are excluded:

| X | Y | R | $R_1$ | $R_2$ |
|---|---|---|---|---|
| $CH_2$ | O | H | $(CH_2)_2 CH_3$ | Ph |
| $CH_2$ | O | H | $CH_3$ | Ph |
| $CH_2$ | O | H | | i-Pr. |

The ACAT inhibitor for use in the novel method may be selected from any effective compound, especially compounds of Formula I above, especially sulfamic acid, [[2,4,6-tris(methylethyl)-phenyl]acetyl]-, 2,6-bis[(1-methylethyl) phenyl ester; 2,6-bis(1-methylethyl)phenyl-[[2,6-bis(1-methylethyl)-phenyl]sulfonyl]carbamate monosodium salt; N-(2,6-di-isopropyl-phenyl)-2-phenyl-malonamic acid dodecyl ester; N-(2,6-diisopropyl-phenyl)-2-(2-dodecyl-2H-tetrazol-5-yl)-2-phenyl-acetamide; 2,2-dimethyl-N-(2,4,6-trimethoxyphenyl)-docecanamide; and N-[2,6-bis(1-methylethyl)phenyl]-N'-[[1-[4-(dimethyl-amino)phenyl] cyclopentyl]methyl urea monohydrochloride.

The doses of ACAT inhibitor contemplated for use in this invention an about 50 to 1500 mg per day, preferably given in single or divided doses.

One especially useful ACAT inhibitor is 2,6-bis(1-methylethyl)phenyl [[2,4,6-tris(1-methylethyl)phenyl] acetyl]sulfamate disclosed in U.S. patent application Ser. No. 08/223,932 filed Apr. 13, 1994, which is hereby incorporated by reference.

Other ACAT inhibitors are 2,6-bis-(1-methylethyl)-phenyl[[2,6-bis(1-methylethyl)phenoxy]-sulfonyl]-carbamate monosodium salt; and similar compounds are disclosed in U.S. Pat. No. 5,245,068; N-(2,6-diisopropyl-phenyl)-2-phenyl-malonamic acid dodecyl ester; and similar compounds are disclosed in U.S. Pat. No. 5,420,339; N-(2,6-diiso-propyl-phenyl)-2-(2-dodecyl-2H-tetrazol-5-yl)-2-phenyl-acetamide; and similar compounds are disclosed in U.S. Pat. No. 5,366,987 and divisional U.S. Pat. No. 5,441,975; N-[2,6-bis(1-methylethyl)phenyl]-N'-[[1-[4-(dimethylamino)phenyl]cyclo-penty]methyl]urea monohydrochloride disclosed in U.S. Pat. No. 5,015,644 and 2,2-dimethyl-N-(2,4,6-trimethoxyphenyl) docecanamide and similar compounds disclosed in U.S. Pat. No. 4,716,175.

The lipid modifying and antiatherosclerotic action of 2,6-bis(1-methylethyl)phenyl[[2,4,6-tris(1-methylethyl)phenyl]acetyl]sulfamate, atorvastatin, and the combination of both compounds was assessed in a rabbit model of atherosclerosis in which the combination of hypercholesterolemia and chronic endothelial denudation of the iliac-femoral artery promotes lesion development The model of atherosclerosis consists of a lesion induction phase of 15 weeks followed by an 8-week drug intervention phase. A main feature of the protocol is that after 9 weeks of a 0.5% cholesterol (C), 3% peanut (PNO), 3% coconut (CNO) oil diet plasma, cholesterol levels are normalized by feeding a 0% C, 3% PNO, 3% CNO diet prior to drug administration. The animals are randomized based on their mean plasma total cholesterol levels and administered the 0% C, 3% PNO, 3% CNO diet either alone or containing N-(2,6-diisopropyl-phenyl)-2 -(2-dodecyl-2H-tetrazol-5-yl)-2-phenyl-acetamide at 10 mg/kg, atorvastatin at 5 mg/kg, or N-(2,6-diiso-propyl-phenyl)-2-(2-dodecyl-2H-tetrazol-5-yl)-2-phenyl-acetamide+atorvastatin at 10+5 mg/kg for the next 8 weeks.

Relative to the untreated, cholesterol-fed control, plasma total cholesterol levels were unchanged by 2,6-bis(1-methylethyl)phenyl[[2,4,6-tris(1-methylethyl)phenyl]acetyl]sulfamate but reduced 43% and 67% with atorvastatin and 2,6-bis(1-methylethyl)-phenyl[[2,4,6-tris(1-methylethyl)phenyl]acetyl]-sulfamate+atorvastatin, respectively. Associated with the changes in plasma total cholesterol were marked alterations in the plasma lipoprotein distribution. 2,6-Bis(1-methylethyl)phenyl[[2,4,6-tris(1-methylethyl)phenyl]acetyl]sulfamate reduced % VLDL-cholesterol (VLDL-C) and increased % LDL-cholesterol (LDL-C); atorvastatin had limited effect; and upon combination treatment % VLDL-C and % LDL-C were reduced, and % HDL-cholesterol was increased.

Results are summarized in Table I below.

TABLE I

Lipoprotein Distribution Expressed as Percent of Total Plasma Cholesterol

|  | VLDL | LDL | HDL |
| --- | --- | --- | --- |
| Progression Control | 16 | 60 | 24 |
| 2,6-bis(1-methylethyl)-phenyl[[2,4,6-tris(1-methylethyl)phenyl]-acetyl]sulfamate (10 mg/kg) | 5 | 73 | 22 |
| Atorvastatin (5 mg/kg) | 14 | 48 | 38 |
| 2,6-bis(1-methylethyl)-phenyl[[2,4,6-tris(1-methylethyl)phenyl]-acetyl]sulfamate + Atorvastatin (10 + 5 mg/kg) | 4 | 35 | 60 |

Analysis of the vascular cholesteryl ester (CE) enrichment, incidence of complex atherosclerotic lesions, gross extent of thoracic aortic atherosclerosis, and size and composition of the iliac-femoral lesion have also been performed. 2,6-Bis(1-methylethyl)phenyl[[2,4,6-tris(1-methylethyl)-phenyl]acetyl]sulfamate had no effect on the CE enrichment of the thoracic aorta and iliac-femoral artery and on the gross extent of lesion coverage in the thoracic aorta; however, the incidence of complex fibrous plaques within the iliac-femoral artery was reduced from 50% to 14%. Atorvastatin reduced the CE enrichment of both vascular regions by 27% to 41% without changing the gross extent of thoracic lesions and incidence of fibrous plaques. 2,6-Bis(1-methylethyl)phenyl[[2,4,6-tris(1-methylethyl)-phenyl]acetyl]sulfamate+atorvastatin had no effect on the CE enrichment of the thoracic aorta and gross extent of thoracic aortic lesions; however, the iliac-femoral CE content was reduced 23% and incidence of fibrous plaques was decreased to 17%. Comparison of the data relative to the time zero control, i.e., prior to drug administration, atorvastatin alone and in combination with 2,6-bis(1-methylethyl)phenyl[[2,4,6-tris(1-methylethyl)phenyl]acetyl]sulfamate significantly reduced the CE enrichment of the iliac-femoral artery Morphometric analysis of the iliac-femoral artery revealed that atorvastatin reduced the lesion size, while the combination of atorvastatin and 2,6-bis(1-methylethyl)phenyl[[2,4,6-tris(1-methylethyl)-phenyl]acetyl]sulfamate significantly decreased the monocyte-macrophage content of the lesion without changing lesion size. 2,6-Bis(1-methylethyl)phenyl[[2,4,6-tris(1-methylethyl)-phenyl]acetyl]sulfamate alone had no effect on the iliac-femoral lesion size or composition.

Therefore, it is clear that a combination of N-(2,6-diisopropyl-phenyl)-2-(2-dodecyl-2H-tetrazol -5-yl)-2-phenyl-acetamide and atorvastatin administered in a chow/fat diet results in a greater reduction in plasma apo B-containing lipoprotein than either alone and that a normalization of the plasma lipoprotein distribution is achieved Atorvastatin not only blunts the cholesteryl ester enrichment of the vasculature but also decrease the lipid enrichment of a pre-existing atherosclerotic lesion. 2,6-Bis(1-methylethyl)phenyl[[2,4,6-tris(1-methylethyl)-phenyl]acetyl]sulfamate+atorvastatin reduces the CE enrichment of pre-existing atherosclerotic lesions to the same extent as atorvastatin alone, but the atherosclerotic lesions are less complicated with respect to their histologic character.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets or transdermal systems are also included.

Tablets, powders, cachets, and capsules can be used as solid dosage forms suitable for oral administration.

Liquid form preparations include solutions, suspensions, or emulsions suitable for oral administration Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form In such form, the preparation is divided into unit doses containing appropriate quantities of the active component. The unit dosage form can be a packaged preparation containing discrete quantities of the preparations for example, packeted tablets, capsules, and powders in vials or ampoules. The unit dosage form can also be a capsule, cachet, or tablet itself, or it can be the appropriate number of these packaged forms.

The dosage forms are well within the skill of a physician who will be familiar with such factors as time of day and other pertinent considerations.

What is claimed is:

1. A method of preventing ischemic sudden death in a patient at risk of the same which comprises administering therapeutically effective amounts of acyl-CoA cholesterol O-acyltransferase (ACAT) inhibitor and an HMG-CoA reductase inhibitor.

2. A method according to claim 1 wherein the ACAT inhibitor is one or more compounds selected from sulfamic acid, [[2,4,6-tris(methylethyl)phenyl]acetyl]-, 2,6-bis[(1-methylethyl)phenyl ester; 2,6-bis(1-methylethyl)phenyl[[2,6-bis(1-methylethyl)phenyl]sulfonyl]carbamate monosodium salt; N-(2,6-diisopropyl-phenyl)-2-phenyl-malonamic acid dodecyl- ester; 5-methoxy-3-(1-methylethoxy)-N-1H-tetrazol-5-ylbenzo[6]thiopheno-2-carboxamide monosodium salt; 2,2-dimethyl-N-(2,4,6-trimethoxyphenyl)-docecanamide; and N-[2,6-bis(1-methylethyl)-phenyl]-N'-[[1-[4-(dimethylamino)phenyl]-cyclopentyl]methyl urea monohydrochloride; and the HMG-CoA reductase inhibitor is one or more compounds selected from rivastatin, lovastatin, simvastatin, pravastatin, fluvastatin, and atorvastatin.

3. A method according to claim 1; wherein the ACAT inhibitor is one or more compounds selected from 2,6-bis (1-methylethyl)-phenyl [[2,4,6-tris-(1-methylethyl)phenyl]-acetyl]sulfamate, N-(2,6-diisopropyl-phenyl)-2-phenyl-malonamic acid dodecyl- ester, and N-(2,6-diisopropylphenyl)-2-(2-dodecyl-2H-tetrazol-5-yl)-2-phenylacetamide; and the HMG-CoA reductase inhibitor is one or more compounds selected from rivastatin, lovastatin, simvastatin, pravastatin, fluvastatin, and atorvastatin.

* * * * *